United States Patent [19]

Kennedy et al.

[11] Patent Number: 5,425,984
[45] Date of Patent: Jun. 20, 1995

[54] BIOABSORBABLE MELT SPUN FIBER BASED ON GLYCOLIDE-CONTAINING COPOLYMER

[75] Inventors: John Kennedy, Stratford; Cheng-Kung Liu, Norwalk, both of Conn.

[73] Assignee: United States Surgical Corporation, Norwalk, Conn.

[21] Appl. No.: 74,135

[22] Filed: Jun. 9, 1993

Related U.S. Application Data

[62] Division of Ser. No. 732,628, Jul. 19, 1991, Pat. No. 5,232,648.

[51] Int. Cl.6 ............................................. D01D 5/12
[52] U.S. Cl. ..................................... 428/229; 528/361; 606/151; 606/230
[58] Field of Search ................. 428/225, 364, 229; 606/139, 151, 230; 528/361

[56] References Cited

U.S. PATENT DOCUMENTS 3,636,956  1/1972  Schneider .......................... 606/230

Primary Examiner—Christopher W. Raimund

[57] ABSTRACT

A bioabsorbable fiber useful for the manufacture of medical devices is obtained from a polymer containing from about 15 to about 30 mole percent glycolide in a melt spinning operation carried out under low shear conditions. The fiber is drawn at a ratio of about 1.5 to 2.7. The fiber possesses excellent tensile strength and a high level of retention of its original strength on storage.

23 Claims, No Drawings

BIOABSORBABLE MELT SPUN FIBER BASED ON GLYCOLIDE-CONTAINING COPOLYMER

This is a divisional of application Ser. No. 07/732,628 filed Jul. 19, 1991 now U.S. Pat. No. 5,232,648.

BACKGROUND OF THE INVENTION

This invention relates to a bioabsorbable melt spun fiber formed from a glycolide-containing polymer, e.g. a lactide-glycolide copolymer.

Polymers and copolymers of, and bioabsorbable surgical devices made from, lactide and/or glycolide and related compounds are well-known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,243,775; 4,273,920; and 4,300,565; U.K. Patent No. 779,291; D. K. Gilding et al., "Biodegradable polymers for use in surgery-polyglycolic/poly(lactic acid) homo and copolymers; 1", *Polymer*, Volume 20, pages 1459-1464 (1979), and D. F. Williams (ed.), *Biocompatibility of Clinical Implant Materials*, Vol. II, ch. 9: "Biodegradable Polymers"(1981). Some of these documents disclose copolymers of lactide and glycolide containing fifteen or more mole percent glycolide. See, e.g., U.S. Pat. Nos. 2,668,162; 2,703,316; 3,297,033; 3,620,218; 3,636,956; 3,736,646; 3,773,919; 3,797,499; 3,839,297; 3,867,190; 3,982,543; and 4,273,920 and the Gilding et al. and Williams (ed.) publications.

By way of example, bioabsorbable composite materials intended for use in medical implantation may include reinforcement fibers enveloped in a matrix. Polymers and copolymers of lactide and/or glycolide can be used as the reinforcement fibers or as amorphous fibers to form the matrix. Such a composite material can be molded into a suitable biomedical implant.

Previously, it has not been possible to produce fibrous material from relatively low glycolide copolymer resins (e.g., 15-20 mole percent glycolide content) having acceptable long-term in vivo tensile strength retention. For example, it is disclosed at line 1 of Table VII in Example XVII of U.S. Pat. No. 3,636,956, that a 20/80 mole percent glycolide/lactide copolymer melt spun into monofilaments has a diameter of 15.9 mils and a straight pull of 9.57 pounds, which gives tensile strength of about 48,000 psi. However, line 1 of Table VIII of this patent documents a greater than 50 percent loss in the in vivo tensile strength over a two week period for this filament composition, i.e. from 10.1 pounds at day zero to 4.0 pounds at 15 days post implant.

SUMMARY OF THE INVENTION

It is a principal object of the invention to provide a bioabsorbable fiber from a glycolide-containing polymer.

It is a more particular object of the invention to provide a bioabsorbable fiber from a glycolide-L-lactide copolymer.

It is a specific object of the invention to provide a bioabsorbable fiber containing a relatively low content of glycolide and possessing a tensile strength at zero time of at least about 70,000 psi.

It is a further specific object of the invention to provide a bioabsorbable fiber containing a relatively low content of glycolide and requiring at least about twelve weeks in vitro at about 37° C. to lose substantially all of its original tensile strength.

It is another object of the invention to provide a bioabsorbable fiber suitable for molding into a desired shape and exhibiting desirably high levels of retention of in vivo tensile strength.

It is still another object of the invention to provide a bioabsorbable fiber exhibiting desirably high levels of retention of in vivo tensile strength and which is suitable as a reinforcement material for surgical devices, such as prostheses, meshes, implants, etc., whether molded, braided, woven, or of other suitable construction.

In keeping with these and other objects of the invention, there is provided a bioabsorbable fiber obtained from a process which comprises melt spinning a polymer in which glycolide content is in the range of from about 15 to about 30 mole percent and inherent viscosity as measured in chloroform at about 30° C. in a concentration of about 0.25 g/dl is at least about 1.0 dl/g at a shear rate not exceeding about 1000 sec$^{-1}$ to provide a bioabsorbable fiber possessing a tensile strength of at least about 70,000 psi at zero time. The glycolide is preferably polymerized with a monomer selected from bioabsorbable materials such as lactide, p-dioxanone, e-caprolactone (epsilon-caprolactone), trimethylene carbonate and mixtures thereof, and which is most preferably L-lactide.

The present invention is also directed to a method for preparing a bioabsorbable fiber, e.g. as described above. Monofilament bioabsorbable surgical fibers prepared as noted above exhibit excellent retention of in vivo tensile strength on storage. For example, fibers prepared in accordance with the present invention possess zero time tensile strength of at least about 80,000 psi, e.g. on the order of about 85,000 to about 115,000 psi, and in vitro retention strength exhibiting less than about a 40 percent loss over about a four week period. Preferably, the bioabsorbable spun fiber retains at least about 80 percent of its tensile strength after about a four week period in vitro (37° C.). The fiber of this invention can be employed in the manufacture of surgical implant devices, notably soft tissue prostheses intended for use in vascular reconstruction, connective tissue repair, etc.

DESCRIPTION OF THE PREFERRED EMBODIMENTS

The bioabsorbable fiber of this invention is obtained from a polymer, preferably a glycolide-L-lactide copolymer, possessing a glycolide content of about 15 to about 30 mole percent, and preferably about 20 mole percent, the balance of the polymer being made up of at least one other bioabsorbable comonomer, preferably L-lactide, and, optionally, quantities of one or more additional monomers copolymerizable with glycolide and L-lactide, e.g., up to a total of about 30 mole percent, preferably up to about 5 mole percent of one or a combination of monomers selected from the group consisting of p-dioxanone, trimethylene carbonate, epsilon-caprolactone, etc. The maximum glycolide content of the polymer is less critical than its minimum level and in general can be as high as about 30 mole percent. However, for optimum fiber properties, it is preferred that the glycolide level not exceed about 25 mole percent.

As noted above, the bioabsorbable comonomer copolymerized with the glycolide is preferably L-lactide. However, other bioabsorbable comonomers could equally be used, such as p-dioxanone, e-caprolactone, trimethylene carbonate and mixtures thereof with or without L-lactide.

In addition to minimum glycolide content, the other characterizing property of the useful polymers is their inherent viscosity as measured in chloroform at about 30° C. in a concentration of about 0.25 g/dl. In general, the inherent viscosity should be at least about 1.0 dl/g, preferably at least about 1.1 dl/g and more preferably at least about 1.3 dl/g, when measured under these conditions. The inherent viscosity of the fiber may be slightly less than that of the bulk polymer due to degradation of the bulk resin occurring within the extruder. Accordingly, where the fiber is to exhibit a given inherent viscosity, it may be advantageous to employ a bulk polymer possessing a somewhat higher inherent viscosity than the target inherent viscosity of the fiber. At the same time, the melt-spun fiber and ultimately-drawn fiber can each exhibit an inherent viscosity of at least about 1.0 dl/g, preferably at least about 1.1 dl/g, and more preferably at least about 1.3 dl/g when measured in chloroform at about 30° C. in a concentration of about 0.25 g/dl.

The foregoing glycolide-containing polymers, e.g. glycolide-L-lactide copolymers, can be prepared in accordance with known techniques. Thus, e.g., they may be prepared following procedures described in such prior art documents as those referred to above.

One suitable polymerization procedure involves heating hydroxyacetic acid (glycolic acid) under nitrogen to 180° C. to remove water. Pressure is then reduced and heating is continued for two hours to yield a prepolymer of polyglycolic acid which is then recovered and powdered.

The polyglycolic acid prepolymer is thereafter heated in the presence of antimony oxide at 275° C. under low pressure with an argon purge and stirring. The prepolymer depolymerizes with the resulting glycolide monomer distilling over and being recovered in a cold vacuum receiver. Any other technique which yields pure enough glycolide monomer can also be used. As will be understood by one skilled in the art, the monomer must be of sufficient purity so that the copolymer will exhibit at least the minimum inherent viscosity as specified above. Preferably, the glycolide monomer is purified by conventional techniques such as distillation, crystallization or sublimation.

L-lactide is used alone or in combination with at most a small amount of the DL racemer. L-lactide can be purified by crystallization from toluene solution or employing some other equally effective purification procedure. The DL racemer, if used, can be purified by crystallization from ethyl acetate or other solvent.

As for the polymerization itself, a mixture of the purified glycolide and e.g., L-lactide monomer, is charged to a reactor under an argon blanket. A suitable catalyst, e.g., a solution of stannous octoate or stannous chloride catalyst in diethyl ether, is added to give about 0.02 wt. percent of catalyst based on the total weight of glycolide and L-lactide. The reactor is further purged with argon and held at about 5 psi while heating to about 170°–175° C. Pressure and temperature are maintained for about six hours.

The reaction product is isolated, comminuted and treated to remove residual reactants. Size of the particles, e.g., in the form of pellets, is usually a few millimeters, e.g. about ½ inch by about 1/16 inch. Particles too small are undesirable. A sufficient amount of unreacted monomer and other impurities is removed so that the resulting polymeric product has at least the inherent viscosity specified above.

Any method capable of removing unreacted monomer from the crude polymer product can be used provided the method results in the polymer having at least the aforementioned minimum inherent viscosity. One suitable purification procedure involves contacting the crude comminuted polymer with ethyl ether for about 72 hours in a Soxhlet-type extractor to remove unreacted monomer(s). Typically, about 4–10 percent of the starting monomer remains unreacted. As will be understood by those skilled in the art, the composition of the copolymer can differ slightly from the composition of the starting monomeric mixture due to the unequal reactivity of the lactide and glycolide.

Following extraction of unreacted monomer(s), the partially purified polymer is slowly heated under vacuum from ambient temperature to about 140° C. over a period of about 48 hours. The slow rate of heating is important to prevent melting (strictly speaking, flowing together) of the polymer particles and to remove any water present. Desirably, dry inert gas, e.g., nitrogen, is used to purge the system and occasionally the heating step may require more than about 48 hours to reach the desired glass transition temperature. The combination of slow heating and purging with dry gas removes any residual solvent (ethyl ether) present thereby raising the glass transition temperature.

After the removal of any unreacted monomer (and solvent if a solvent extraction procedure was used), the purified polymer is dried if it was not dried sufficiently in the monomer removal step. If the polymer is to be stored prior to melt spinning, it should be stored under essentially anhydrous conditions to avoid undue decomposition during such storage. The polymer must be as dry as possible before melt spinning because the presence of an excessive amount of water in the polymer will result in the inherent viscosity dropping below the minimum acceptable level during the melt spinning operation. Generally, it is desired that the polymer be stored at a relative humidity of no more than a few percent. Preferably, the purified dried polymer is stored under a vacuum and/or with a dry inert gas purge.

Employing the melt spinning conditions hereinafter described, the bulk polymer, e.g. glycolide-L-lactide copolymer, is formed into a final drawn fiber ranging in denier from about 1.2 to about 3.0 and preferably from about 1.5 to about 2.0.

A critical requirement of the melt spinning operation (in addition to the inherent viscosity specification of the bulk copolymer) is that it be carried out at a shear rate not exceeding about 1000 $sec^{-1}$ and preferably not above about 500 $sec^{-1}$. Known melt spinning equipment operating in accordance with known techniques can be utilized to process the bulk polymer into the fiber of this invention. Table I below sets forth approximate ranges of conditions for each aspect of the melt spinning operation:

TABLE I

| MELT SPINNING CONDITIONS | | |
| --- | --- | --- |
| | Broad Range | Preferred Range |
| Spinneret Orifice Diameter, mm | 0.30–0.70 | 0.45–0.55 |
| Extruder Screw Length to Diameter Ratio | 12:1–24:1 | 15:1–20:1 |
| Throughput at the Spinneret | 0.10–0.40 | 0.19–0.30 |

TABLE I-continued

| MELT SPINNING CONDITIONS | | |
|---|---|---|
| | Broad Range | Preferred Range |
| Orifice, cc/min. | | |
| Extrusion Temperatures, °C. | | |
| Barrel Zone No. 1 | 150–190 | 155–170 |
| Barrel Zone No. 2 | 160–190 | 165–180 |
| Adapter | 160–180 | 165–175 |
| Block | 170–190 | 175–185 |
| Pump | 170–190 | 175–185 |
| Die | 180–200 | 185–195 |
| Barrel Melt | 165–190 | 170–185 |
| Pump Melt | 175–195 | 180–190 |
| Die Melt | 175–195 | 180–190 |
| Chimney | 65–100 | 70–90 |
| Chimney Air | 65–95 | 75–85 |
| Extrusion Pressures, psi | | |
| Barrel | 200–1500 | 900–1200 |
| Pump | 200–1500 | 500–1200 |
| Die | 400–1000 | 550–900 |
| First Take-Up Godet Speed, m/min | 300–600 | 400–500 |

As the fiber emerges from the spinneret, it is drawn to orient the polymer and increase its tensile strength. Approximate drawing conditions which can be utilized herein with generally good results are set forth in Table II as follows:

TABLE II

| DRAWING CONDITIONS OF THE AS-SPUN FIBER | | |
|---|---|---|
| | Broad Range | Preferred Range |
| Oven temperature, °C. | 95–125 | 100–110 |
| Transit Time, sec. | 1.0–3.0 | 1.3–2.0 |
| Draw Ratio | 1.5–2.7 | 1.6–2.5 |
| Draw Speed (Final Godet Speed), m/min. | 20–200 | 60–150 |

The drawing can be conducted in one or more steps, in air or in a bath containing a liquid nonsolvent for the polymer, e.g., glycerol or water. Following drawing, the fiber can be subjected to an optional annealing operation by running the fiber from a feed roll to a takeup roll and heating the fiber between the rolls, with the takeup roll rotating at a speed which ranges from the same speed as the feed roll to a speed which is about 4 percent slower than that of the feed roll. At the first-mentioned speed ratio, essentially no shrinkage will take place and at the second-mentioned speed ratio shrinkage will take place up to about 4 percent of its length. As a consequence of this annealing, the fiber will resist shrinkage when implanted within a body.

The filaments can be interwoven, knitted or braided with filaments of different chemical composition, to provide optimum bioabsorption characteristics. For example, the glycolide-containing filament can be interwoven, knitted, or braided with filaments formed from a composition containing a greater amount of glycolide, e.g. on the order of about 60 to about 80 mole percent glycolide, and about 20 to 40 mole percent L-lactide. Generally, lactide is absorbed more slowly in, vivo than glycolide, while glycolide provides more tensile strength than lactide. Accordingly, by interweaving, knitting, or braiding threads having such differing compositions, a composite having the optimum desired properties can be prepared.

Furthermore, the filaments prepared above can be interwoven, knitted, or braided with filaments formed from non-bioabsorbable polymers, such as polyolefins including polyethylene homopolymers, polypropylene homopolymers, ethylene propylene copolymers, ethylene propylene terpolymers, etc., fluorinated hydrocarbons, fluorosilicones, isobutylenes, isoprenes, polyacrylates, polybutadienes, polyurethanes, polyether polyester copolymers, and the like. Hytrel (Du Pont), a family of copolyester elastomers based on (soft) polyether segments and (hard) polyester segments, and spandex, an elastomeric segmented polyurethane can be spun into filaments and interwoven, knitted, or braided with the glycolide-containing filaments spun as described above, to provide composites having optimum biocompatible characteristics.

Still further, the as spun and/or drawn filaments can be used to form molded articles, with the drawn filaments providing reinforcement to the molded articles to improve the strength characteristics thereof.

The bioabsorbable filament prepared in accordance with the present invention comprises a glycolide content of from about 15 to about 30 mole percent, has a tensile strength of at least about 70,000 psi at zero time, and requires at least about 12 weeks in vitro at 37° C. to lose substantially all of its original tensile strength.

The following examples are illustrative of bioabsorbable multifilament fibers melt spun in accordance with the present invention:

EXAMPLES 1–5

Five separate bioabsorbable multifilament fibers 1–5 were prepared according to the melt spinning and drawing procedures described above and under the conditions outlined in Table III below. Multifilament fibers 1–5 were each composed of approximately 20 mole percent glycolide and approximately 80 mole percent L-lactide. Properties of the respective spun fibers 1–5 are also given in Table III below:

TABLE III

| | 1 | 2 | 3 | 4 | 5 |
|---|---|---|---|---|---|
| Inherent Viscosity of Resin[1] (dl/g) | 1.45 | 1.31 | 1.38 | 1.36 | 1.41 |
| Melt Spinning Conditions | | | | | |
| Spinneret Orifice Diameter (mm.) | 0.36 | 0.36 | 0.50 | 0.50 | 0.50 |
| Number of Spinneret Orifices | 26 | 26 | 24 | 32 | 26 |
| Extruder Screw Length to Diameter Ratio | 15:1 | 15:1 | 15:1 | 15:1 | 15:1 |
| Throughput at the Spinneret Orifice (cc/min.) | 0.13 | 0.13 | 0.18 | 0.19 | 0.22 |
| Extrusion Temperatures (°C.) | | | | | |
| Barrel zone No. 1 | 175 | 177 | 189 | 160 | 170 |
| Barrel zone No. 2 | 180 | 180 | 182 | 170 | 173 |
| Adapter | 180 | 180 | 180 | 170 | 173 |
| Block | 180 | 180 | 180 | 180 | 173 |
| Pump | 180 | 180 | 180 | 180 | 173 |
| Die | 186 | 181 | 190 | 190 | 182 |
| Barrel Melt | 185 | 183 | 188 | 175 | 177 |

TABLE III-continued

|  | 1 | 2 | 3 | 4 | 5 |
| --- | --- | --- | --- | --- | --- |
| Pump Melt | 184 | 183 | 185 | 183 | 179 |
| Die Melt | 188 | 189 | 190 | 186 | 184 |
| Chimney | 70 | 69 | 73 | 85 | 84 |
| Chimney Air | 78 | 77 | 69 | 80 | 79 |
| Extrusion Pressures (psi) | | | | | |
| Barrel | 900 | 240 | 741 | roughly 754–1107 | 1067 |
| Pump | 800 | 270 | 431 | roughly 193–513 | 933 |
| Die | 857 | 732 | 430 | roughly 463–471 | 790 |
| First Take-Up Godet Speed (m/min.) | 412 | 400 | 434 | 487 | 544 |
| Properties Of The As-Spun Fibers | | | | | |
| Denier per Filament | 3.15 | 3.19 | 3.77 | 3.59 | 3.71 |
| Tenacity (g/d) | >1.5 | >1.5 | >1.5 | >1.5 | >1.5 |
| Elongation (%) | >50 | >50 | >50 | >50 | >50 |
| Inherent viscosity (dl/g) | roughly 1.23–1.45 | roughly 1.12–1.46 | roughly 1.24–1.25 | roughly 1.24–1.32 | roughly 1.21–1.37 |
| Drawing Conditions of the As-Spun Fiber | | | | | |
| Oven Temperature (°C.) | roughly 105–109 | roughly 105–109 | roughly 105–107 | 105 | roughly 105–110 |
| Transit Time (sec) | 2.0 | 2.0 | 1.3 | 1.4 | 1.8 |
| Draw Ratio | roughly 1.64–1.67 | roughly 1.68–1.72 | roughly 2.21–2.27 | 2.15 | roughly 1.97–2.03 |
| Draw Speed (Final Godet Speed) (m/min) | roughly 68.6–69.1 | roughly 70.0–71.5 | roughly 88.7–150.0 | roughly 26.2–26.8 | roughly 81.1–82.3 |
| Properties of The Drawn Fibers | | | | | |
| Denier Per Filament | 1.88 | 1.86 | roughly 1.66–1.75 | roughly 1.63–1.68 | roughly 1.86–1.93 |
| Tenacity (g/d) | roughly 5.59–6.13 | roughly 5.07–5.57 | roughly 5.1–5.6 | roughly 5.6–6.7 | roughly 5.0–6.3 |
| Elongation (%) | roughly 21.3–22.4 | roughly 22.5–24.2 | roughly 15–18 | roughly 14–18 | roughly 18–24 |
| Inherent Viscosity[1] (dl/g) | roughly 1.11–1.36 | roughly 1.15–1.32 | roughly 1.22–1.35 | roughly 1.21–1.39 | roughly 1.24–1.29 |

[1]Measured in chloroform at 30° C. and 0.25 g/dl concentration.

In vitro knot pull strength characteristics for three separate drawn Fibers I, II and III prepared in accordance with the present invention were analyzed, with the results reported in Table IV below:

TABLE IV

KNOT PULL STRENGTH

| | | | KNOT PULL STRENGTH RECORDED AFTER NUMBER OF WEEKS | | | | | | | | |
| --- | --- | --- | --- | --- | --- | --- | --- | --- | --- | --- | --- |
| FIBER | FIBER COMPOSITION | Immediately Upon Fabrication Kg | After 2 Weeks[2] | | After 4 Weeks[2] | | After 6 Weeks[2] | | After 8 Weeks[2] | | After 12 Weeks[2] |
| | | | Kg | % Remaining | Kg | % Remaining | Kg | % Remaining | Kg | % Remaining | Kg | % Remaining |
| I | approx. 20/80 mole % glycolide/L-lactide | 0.998 | 0.876 | 87.8 | — | — | 0.646 | 64.7 | — | — | 0.220 | 22.0 |
| II | approx. 20/80 mole % glycolide/L-lactide[3] | 0.967 | 0.924 | 95.6 | 0.903 | 93.4 | 0.871 | 90.1 | — | — | 0.450 | 46.5 |
| III | approx. 20/80 mole % glycolide/L-lactide | 4.032 | 3.304 | 81.8 | 2.524 | 62.3 | — | — | 1.593 | 39.5 | 0.710 | 17.61 |

[2]Stored in Sorenson's buffer solution at 37° C. to simulate in vivo conditions.
[3]Treated with heat and vacuum to remove unreacted monomers.

In vitro knot pull strength retention is indicative of in vivo strength retention. A fiber of like composition and comparable diameter to Fiber III (size 0) in Table IV supra is reported in Table VII of U.S. Pat. No. 3,636,956 to Schneider (15.4 mils and 15.9 mils respectively). The Schneider fiber exhibits a dry knot pull strength at zero time of 5.96 lbs., which equates to approximately 2.7 kgs. By contrast, as shown in Table IV hereinabove, Fiber III exhibits an initial knot pull strength of 4,032 kgs, i.e., an initial knot pull strength roughly 50 percent greater than the Schneider fiber.

Thus, Fiber III obtained in accordance with the present invention as documented in Table IV above significantly outperforms the fiber described in Table VII of U.S. Pat. No. 3,636,956 which was similarly obtained from a glycolide-L-lactide copolymer containing 20 mole percent glycolide. While the Schneider fiber showed a greater than 50 percent loss in its original in vivo tensile strength (under accelerated aging conditions) of two weeks (Table VIII in U.S. Pat. No. 3,636,956), Fiber III of the present invention lost less than 40 percent of its initial in vitro knot pull strength after a four week storage period (and less than 10 percent loss in this period for Fiber II) under essentially the same conditions. In other words, the bioabsorbable melt spun and drawn fiber documented as Fiber III above retained at least about 60 percent of its original tensile strength after a four week period in vitro at 37° C.

Although in vivo tensile strength and in vitro knot pull strength are not identical measures, comparison between in vivo tensile strength retention and in vitro knot pull strength retention are instructive in evaluating the relative strength retention properties, e.g., in vivo, of various materials. Additionally, since the tenacity unit of 1 g/denier is roughly equal to about 17,800 psi, the drawn fibers 1–5 from Table III all possess tensile strengths well over 70,000 psi, i.e. on the order of about 89,000 to about 119,000 psi.

What is claimed is:

1. A bioabsorbable filament drawn at a ratio of about 1.5 to 2.7, in which glycolide content is in the range of from about 15 to about 30 mole percent, said filament having a tensile strength of at least about 70,000 psi at zero time.

2. The bioabsorbable filament of claim 1, comprising a glycolide content of about 20 mole percent.

3. The filament of claim 1 which is drawn at a ratio of about 1.6 to 2.5.

4. A bioabsorbable fiber obtained from a process which comprises melt spinning a polymer in which glycolide content is in the range of from about 15 to about 30 mole percent and inherent viscosity as measured in chloroform at about 30° C. in a concentration of about 0.25 g/dl is at least about 1.0 dl/g at a shear rate not exceeding about 1,000 sec$^{-1}$, and drawing the thus spun fiber at a ratio of about 1.5 to 2.7, to provide a bioabsorbable melt spun fiber possessing a tensile strength of at least about 70,000 psi at zero time.

5. The bioabsorbable fiber of claim 4 wherein the glycolide content of the polymer is about 20 mole percent.

6. The bioabsorbable fiber of claim 5 wherein the inherent viscosity of the polymer is at least about 1.3 dl/g as measured in chloroform at about 30° C. in a concentration of about 0.25 g/dl.

7. The bioabsorbable fiber of claim 4 wherein the inherent viscosity of the polymer is at least about 1.1 dl/g as measured in chloroform at about 30° C. in a concentration of about 0.25 g/dl.

8. The bioabsorbable fiber of claim 4 wherein the shear rate of the melt spinning does not exceed about 500 sec$^{-1}$.

9. The bioabsorbable fiber of claim 4 possessing a tensile strength of at least about 80,000 psi.

10. The bioabsorbable fiber of claim 4, in which the glycolide is polymerized with a comonomer selected from the group consisting of lactide, p-dioxanone, e-caprolactone, trimethylene carbonate and mixtures thereof.

11. The bioabsorbable fiber of claim 10, in which the glycolide is copolymerized with L-lactide.

12. The bioabsorbable fiber of claim 4 wherein fiber is drawn at a ratio of about 1.6 to 2.5.

13. A bioabsorbable fiber obtained from a process which comprises melt spinning a polymer in which glycolide content is in the range of from about 15 to about 30 mole percent at a shear rate not exceeding about 1,000 sec$^{-1}$, and drawing the thus spun fiber at a ratio of about 1.5 to 2.7, to provide a bioabsorbable melt spun fiber possessing a tensile strength of at least about 70,000 psi at zero time and an inherent viscosity, as measured in chloroform at about 30° C. in a concentration of about 0.25 g/dl, of at least about 1.0 dl/g.

14. The bioabsorbable fiber or claim 13 wherein said fiber is drawn at a ratio of about 1.6 to 2.5.

15. A bioabsorbable fiber obtained from a process which comprises melt spinning a polymer in which glycolide content is in the range of from about 15 to about 30 mole percent and inherent viscosity as measured in chloroform at about 30° C. in a concentration of about 0.25 g/dl is at least about 1.0 dl/g at a shear rate not exceeding about 1,000 sec$^{-1}$, and drawing the thus spun fiber at a ratio of about 1.5 to 2.7, to provide a bioabsorbable melt spun fiber possessing a tensile strength of at least 70,000 psi at zero time, and retaining at least about 80% of its tensile strength after about a four week period in vitro at about 37° C.

16. The fiber of claim 15 which is drawn at a ratio of about 1.6 to 2.5.

17. A bioabsorbable drawn fiber obtained from a process which comprises melt spinning a polymer in which glycolide content is in the range of from about 15 to about 30 mole percent at a shear rate not exceeding about 1,000 sec$^{-1}$ to provide a bioabsorbable melt spun fiber and then drawing said melt spun fiber at a ratio of about 1.5 to 2.7, to provide a drawn fiber possessing a tensile strength of at least about 70,000 psi at zero time and an inherent viscosity, as measured in chloroform at about 30° C. in a concentration of about 0.25 g/dl, of at least about 1.0 dl/g.

18. The bioabsorbable drawn fiber of claim 17, wherein said fiber is drawn at a ratio of about 1.6 to 2.5.

19. A bioabsorbable surgical article manufactured from a plurality of fibers, at least one of said fibers being produced by a process which comprises melt spinning, at a shear rate not exceeding about 1,000 sec$^{-1}$, a polymer containing from about 15 to about 30 mole percent glycolide, and drawing the melt spun fiber at a ratio of about 1.5 to 2.7 to orient the polymer and increase tensile strength thereof, whereby a bioabsorbable melt spun fiber possessing a tensile strength of at least about 70,000 psi at zero time is prepared.

20. The article 19 wherein the fiber is drawn at a ratio of about 1.6 to 2.5.

21. The article of claim 19 wherein said article is a mesh.

22. The article of claim 21 wherein said mesh is knitted or woven.

23. The bioabsorbable article of claim 19 "wherein the also comprises fibers formed from non-bioabsorbable polymers".

* * * * *